United States Patent [19]
Lee et al.

[11] Patent Number: 5,908,777
[45] Date of Patent: Jun. 1, 1999

[54] LIPIDIC VECTOR FOR NUCLEIC ACID DELIVERY

[75] Inventors: Robert J. Lee, Pittsburgh; Leaf Huang, Wexford, both of Pa.

[73] Assignee: University of Pittsburgh, Pittsburgh, Pa.

[21] Appl. No.: 08/494,296

[22] Filed: Jun. 23, 1995

[51] Int. Cl.⁶ .................................................. C12N 15/63
[52] U.S. Cl. ................................. 435/320.1; 435/172.1; 435/172.3; 435/69.1; 435/325; 514/44; 424/93.21
[58] Field of Search .......................... 514/44; 435/172.3, 435/69.1, 325, 320.1, 172.1; 424/93.21

[56] References Cited

FOREIGN PATENT DOCUMENTS

| 0 424 688 | 9/1990 | European Pat. Off. . |
| 497 997 A1 | 8/1992 | European Pat. Off. . |
| WO 93/07283 | 4/1993 | WIPO . |

OTHER PUBLICATIONS

Feero et al. "Selection and use of ligands of receptor–mediated gene delivery to myogenic cells", Gene Therapy (1997) 4, 664–674.
Gao et al. "Potentiation of Cationic Liposome–Mediated Gene Delivery by Polycations", Biochemistry 1996, 35, 1027–1036 (Received Oct. 12, 1995).
C. Wang et al., "Polyhistidine Mediates an Acid–Dependent Fusion Of Negatively Charged Lipsomes" Biochemistry, vol. 23, No. 19, 1984, pp. 4409–4416.
A. V. Kabanov et al., "Efficient Transformation of Mammalian Cells Using DNA Interpolyelectrolyte Complexes with Carbon Chain Polycations", Bioconjugate Chemistry, vol. 4, No. 6, 1993,pp. 458–454.
R. Lee et al., "Folate–Targeted, Anionic Liposome–Entrapped Polylysine–Condensed DNA for Tumor Cell–Specific Gene Transfer", Journal of Biological Chemistry, vol. 271, No. 14, pp. 8481–8487.
S. Li et al., "Lipid Supramolecular Assemblies for Gene Transfer", Journal of Liposome Research vol. 6, No. 3, 1996, pp. 589–608.
Schreier "Lipsome Aerosols", J. Liposome Research 2(2): 145–184 (1992).
Zhou et al. "Improved Encapsulation of DNA in pH–Sensitive Liposomes for Transfection", J. Liposome Research 2(1): 125–139 (1992).
Chu et al. "Efficiency of Cytoplasmic Delivery by pH–Sensitive Liposome to Cells in Culture", Pharmaceutical Research, 7(8): 824–834 (1990).
Lee et al. "Delivery of Lipsomes into Cultured KB Cells via Folate Receptor–mediated Endocytosis", J. Biological Chemistry 269(5): 3198–3204 (1994).
Stegmann et al. "Protein–mediated Membrane Fusion", Annu. Rev. Biophys. Chem. 18: 187–211 (1989).
Weber et al. "Evidence for H+ –induced Insertion of Influenza Hemagglutinin HA2 N–terminal Segment Into Viral Membrane", J. Biological Chem. 269(28): 18353–18358 (1994).
Heensler et al. "Polyamidoamine Cascade Polymers Mediate Efficient Transfection of Cells in Culture", Bioconjugate Chem. 4: 372–379 (1993).
Goldfarb et al. "Synthetic Peptides as Nuclear Localization Signals", Nature, 322(14): 641–644 (1986).
Gao et al. "A Novel Cationic Liposome Reagent for Efficient Transfection of Mammalian Cells", Biochemical and Biophysical Research Communications 179(1): 280–285 (1991).
Orkin et al., Report and Recommendations of the Panel to Assess the NIH Investment in Research on Gene Therapy, Dec. 7, 1995.
Lee et al., Biochimica Et Biophysica Acta, vol. 1233:2, pp. 134–144, Feb. 15, 1995.
Remy et al., Proceedings of the National Academy of Sciences of the U.S.A., vol. 92:5, pp. 1744–1748, Feb. 28, 1995.

Primary Examiner—Deborah Crouch
Assistant Examiner—Jill D. Schmuck
Attorney, Agent, or Firm—Foley & Lardner

[57] ABSTRACT

A simple, rapid method for creating a lipidic vector for delivery of a therapeutic molecule entails bringing the molecule into contact with a polycation, thereby forming a complex, and then mixing the complex with an anionic lipidic preparation. Tissue-specific targeting peptides, fusogenic peptides and nucleus-targeting peptides also can be added to the lipid preparation. The result is a stable lipidic vector of reduced immunogenicity and cytotoxicity. The vector also displays enhanced transfection activity.

11 Claims, 6 Drawing Sheets

LIPIDIC VECTOR FOR NUCLEIC ACID DELIVERY

BACKGROUND OF THE INVENTION

The growing field of genetic therapy requires methodology for delivering nucleic acids, synthetic or natural, in the form of DNA, RNA or oligonucleotides containing modified nucleotides, to cells of an organism. The method of delivery can be diverse, and includes use of viruses, direct injection of "naked" DNA into the organism, ex vivo introduction of nucleic acids to cells by chemical-mediated transformation of the cells or electroporation, or use of liposomes.

Non-viral vectors such as liposomes recently have attracted attention as possible vehicles for nucleic acid delivery in gene therapy. In relation to viral vectors, liposomes are safer, have higher capacity, are less toxic, and are non-immunogenic. Felgner, P. L. and Ringold, G. M., Nature 337, 387–388 (1989). Among these vectors, cationic liposomes are the most studied, due to their effectiveness in mediating mammalian cell transfection in vitro. The technique, known as lipofection, employs a liposome made of nucleic acid/cationic lipid and facilitate transfection into cells. The lipid-nucleic acid complex fuses or otherwise disrupts the plasma or endosomal membranes and efficiently transfers the nucleic acid into cells. Lipofection is five to one hundred times more efficient in introducing DNA into cells than calcium phosphate or DEAE-dextran transfection methods. Chang et al., Focus 10: 66 (1988).

Cationic liposome preparations can be made by conventional methodologies. See, for example, Felgner et al., Proc. Nat'l Acad. Sci USA 84:7413 (1987); Schreier, J. of Liposome Res. 2:145 (1992); Chang et al. (1988), supra. Commercial preparations, such as Lipofectin® (Life Technologies, Inc., Gaithersburg, Md. USA), also are available. The amount of liposomes and the amount of DNA can be optimized for each cell type based on a dose response curve. Felgner and Ringold (1989), supra.

Cationic lipids are not found in nature, and DNA/cationic liposomes complexes remain quite cytotoxic, as these complexes appear incompatible with the physiological environment in vivo which is rich in anionic molecules. They may also have undesirable non-specific interactions with negatively charged serum components, blood cells, and the extracellular matrix in vivo.

Another serious limitation in the use of DNA/cationic liposome complexes has been the lack of success in targeting these complexes by use of tissue-specific ligands. This is probably due to the presence of cationic charge in the complex which leads to excessive non-specific tissue uptake.

When cationic liposomes are used as DNA vectors, DNA is complexed with the liposomes via charge interaction. Since DNA usually cannot be optimally condensed by cationic liposomes, the DNA/liposome complex is unstable, i.e., it undergoes slow aggregation. The aggregation increase at high DNA concentration, which is required for clinical applications. Therefore, DNA/cationic liposome complexes need to be prepared fresh, which reflects in increased cost and decreased convenience.

Anionic liposomal vectors have also been examined. These include pH sensitive liposomes which disrupt or fuse with the endosomal membrane following endocytosis and endosome acidification. With conventional technology, DNA encapsulation with anionic liposomes requires very high lipid concentration and entrapment efficiency rarely exceeds 20%. Only a small portion of the liposomes generated contains DNA. The poor DNA encapsulation efficiency achieved by conventional methods is due in large part to the relatively large size of uncondensed DNA and its inability to interact with the anionic liposomes. Procedures commonly used to increase liposomal entrapment efficiency, such as repeated freeze-thaw cycles and polycarbonate membrane extrusion can also lead to severe damage to the DNA strands and loss of DNA expression activity. Zhou, X., Klibanov, A. L., and Huang, L., J. Lip. Res. 2: 125–39 (1992).

Other non-liposomal lipidic vectors, both cationic and anionic, such as oil-in-water emulsions and micelles composed of various anionic, non-ionic or cationic surfactants or surfactant mixtures, also potentially can complex with DNA and mediate DNA delivery. These vectors share many of the same problems associated with liposomal vectors, such as non-specific uptake, cytotoxicity and low encapsulation efficiency.

DNA/liposome complexes are sometimes targeted to the cell type or tissue of interest by the addition to the liposome preparation of a ligand, usually a polypeptide, for which a corresponding cellular receptor has been identified. An example of a cell receptor that can be targeted is the folate receptor which has recently been identified as a prominent tumor marker, especially in ovarian carcinomas. KB cells are known to vastly overexpress the folate receptor. Campbell et al., Cancer Res. 51: 6125–6132 (1991). Yet other targeting ligands have been examined for liposome targeting including transferrin, protein A, ApoE, P-glycoprotein, $\alpha_2$-macroglobin, insulin, asiolofetuin, asialoorosomucoid, monoclonal antibodies with a variety of tissue specificity, biotin, galactose or lactose containing haptens (monovalent and tri-antennary), mannose, dinitrophenol, and vitamin B12. The ligands are covalently conjugated to a lipid anchor in either pre-formed liposomes or are incorporated during liposome preparation. Lee and Low J. Biol. Chem. 269: 3198–3204 (1994) and Lee and Low Biochim. Biophys. Acta 1233: 134–144 (1995).

Synthetic peptides could be incorporated into DNA/liposome complexes to enhance their activity, or to target them to the nucleus. For example, in order to gain access to the cytoplasm, the DNA molecule must overcome the plasma membrane barrier. In nature, viral fusion peptides facilitate the delivery of viral DNA into the cytoplasm by promoting viral membrane fusion with the plasma membrane. For recent reviews on this subject see Stegmann et al., Ann. Rev. Biophys. Chem. 18: 187–221 (1989). For the influenza virus, the hemagglutinin (trimer) HA peptide N-terminal segment (a hydrophobic helical sequence) is exposed due to a conformational change induced by acidic pH in the endosomes (pH 5–6), inserts into the target membrane, and mediates the fusion between the virus and the target endosomal membrane. Weber et al., J. Biol. Chem. 269: 18353–58 (1994). Recently, several amphipathic helix-forming oligopeptides have been designed to imitate the behavior of the viral fusion peptide. See, for example, Haensler and Szoka, Bioconj. Chem. 4: 372–79 (1993). Existing technology for use of these peptides require either the covalent conjugation of the peptide to a DNA-binding molecule such as a polycation (for an example see Haensler and Szoka, supra, or the inclusion in the transfection medium of a high concentration of the peptides. The disadvantage of covalent conjugation of peptides to a polycation is that the formation of a high molecular weight conjugate is known to invoke an immune response (including T-cell and antibody responses) against the peptide in vivo. While free oligopeptides are generally non-immunogenic, maintaining a high peptide concentration in the medium is prohibitively expensive and incompatible with in vivo gene therapy.

Expression of DNA into a protein product in mammalian cells requires that transcription of DNA into mRNA takes place in the nucleus. Therefore, the DNA moiety in the liposome of the invention needs to cross the nuclear envelope for the expression of said DNA inside a cell. Nuclear localization signal peptides, when attached covalently to a macromolecule such as a protein, have been shown to facilitate their translocation into the nucleus. Goldfarb et al., *Nature* 322: 641–44 (1986); Shreiber et al., *Med. Sci.* 8: 134–39 (1992). It has been proposed that this could also be used to facilitate delivery of liposome contents. Again, the disadvantage of covalent conjugation of peptides to a polycation is that the formation of a high molecular weight conjugate is known to invoke an immune response, including T-cell and antibody responses, against the peptide in vivo.

SUMMARY OF THE INVENTION

Accordingly, it is an object of the present invention to provide a lipidic vector, for delivery of nucleic acid and other molecules of therapeutic value, that is less cytotoxic, induces less the immune response, is less prone to aggregation and, hence, delivers a higher concentration of nucleic acid. The vector has a higher transfection efficiency than lipidic vectors produced by conventional methods.

It is also an object of the present invention to provide a method for producing a lipidic vector that is easily and rapidly assembled, does not generate substantial quantities of empty vectors and therefore does not require a step to remove these empty vectors and which is less disruptive of nucleic acid components than are known techniques.

It is yet another object of the present invention to provide a fusogenic peptide, suitably used in the aforementioned method, that enhances transfection of cells by means of the lipidic vector.

In accomplishing these and other objects, there has been provided, in accordance with one aspect of the present invention, a method for creating a lipidic vector for delivering a nucleic acid, which method comprises the steps of (A) providing a polycation and an anionic lipidic preparation, respectively; (B) combining the therapeutic molecule with one entity of the polycation and the anionic lipidic preparation such that a complex is formed; and (C) mixing the complex with the other entity to form the lipidic vector. In a preferred embodiment, a ligand is added to the lipidic vector (i) by covalently bonding the ligand to the lipidic preparation or to the polycation molecule, or (ii) by mixing the ligand with the lipidic preparation or the nucleic acid/polycation complex. In another preferred embodiment, step (B) comprises combining with the therapeutic molecule a first entity that drives surface charge away from neutrality in the reaction mixture. In yet another preferred embodiment, the method further comprises, after step (B) and before step (C), the step of adding to the reaction mixture a second entity that substantially neutralizes any charge on the complex.

In accordance with another aspect of the present invention, a lipidic vector for nucleic acids delivery is provided that is the product of the above-described method.

There also has been provided, pursuant to yet another aspect of the present invention, a fusogenic peptide that is suitably employed in the method described above and that has the amino acid sequence GLFGAIAGFIESILELALEL (SEQ ID NO:1).

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The present invention provides a lipidic vector which offers numerous benefits over conventional vectors, and which is produced via a method that itself has several specific advantages. In accordance with one aspect of the present invention, charge-based interactions are exploited (A) to combine a therapeutic molecule with a polycation, (B) to combine the polycation with an anionic lipidic preparation and, optionally, (C) to introduce a ligand, all in order to control the surface charge of the vector and thereby reduce the above-mentioned, non-specific in vivo associations, and to enhance transfectability of targeted cells. In accordance with the present invention, the therapeutic molecule/ polycation complex can be quantitatively incorporated into a lipidic vector.

The lipidic vector of the present invention can be used to deliver nucleic acids as well as other types of molecules having therapeutic value. Illustrative of such therapeutic molecules are drugs, e.g., hormones, growth factors, secondary metabolites and synthetic pharmaceutical compounds, and antigenic substances useful for raising an immune response. The therapeutic molecule is included in the lipidic vector via charge interaction with the polycation, as in the case of a nucleic acid, or via conjugation, i.e., by covalent bonding of the therapeutic molecule to the polycation or to a lipid of the lipidic preparation. The covalent bonding can be achieved by conventional methods.

Preparation of the vector can include the addition of cellular receptor-targeting ligands, fusogenic ligands, nucleus-targeting ligands, or a combination of such ligands, either to the lipidic preparation, to the polycation molecule, or to the complex formed with the therapeutic molecule. "Ligand" here denotes a molecule, which is often a peptide, that facilitates connection between a cell or a cellular nucleus and the lipidic vector or the encapsulated complex.

Figure 1:
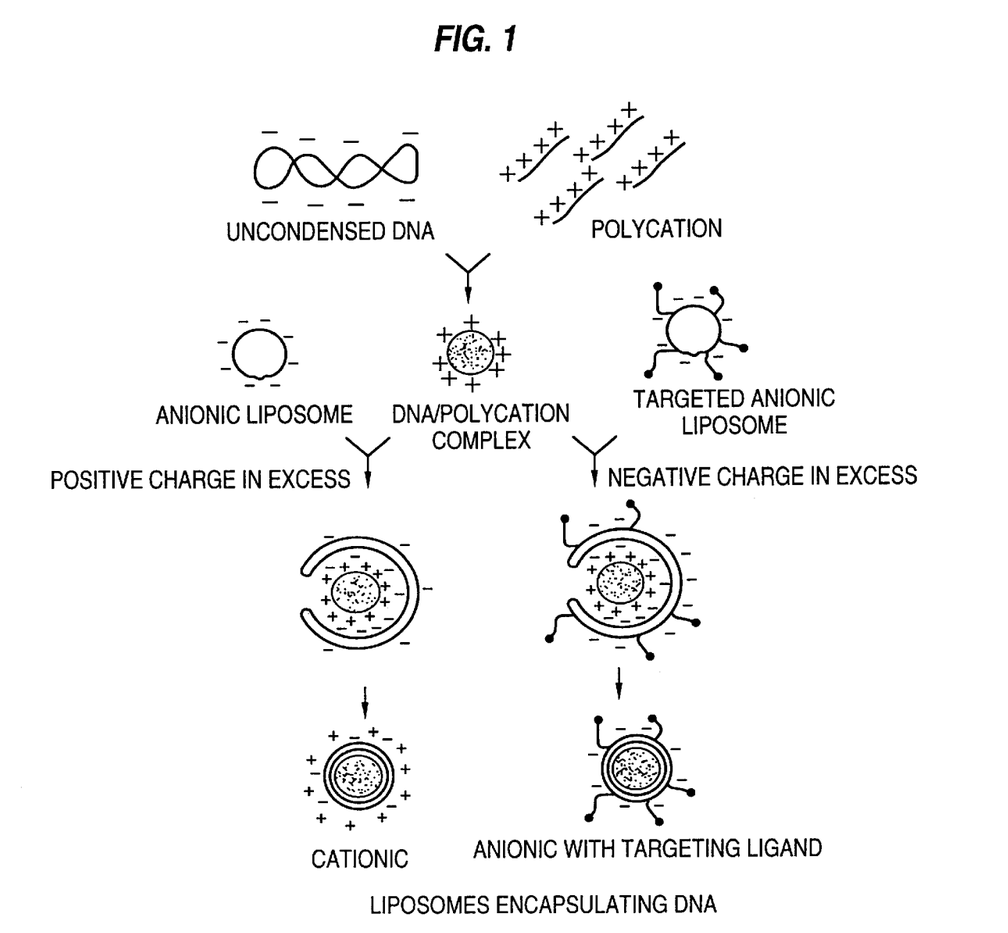
FIG. 1 is a scheme showing the principle and steps involved in preparation of Liposome Encapsulating DNA vectors (lipidic vectors), according to the invention.

FIG. 1 depicts schematically the sequence of events and the principles involved in production of a lipidic vector within the present invention. Thus, a therapeutic molecule, which is DNA in FIG. 1, is mixed with a polycation so that an excess of positive charge occurs, efficiently condensing the DNA in a DNA/polycation complex. Since the nucleic acid in this vehicle is highly condensed, it is more resistant to nuclease activity.

According to FIG. 1, after formation of the DNA/polycation complex, the condensed complex is brought into contact with the anionic lipidic preparation. As a result, DNA-encapsulating lipidic vectors are obtained which vary in overall charge as a function of the ratio of DNA/polycation to lipidic preparation.

This charge variation is important generally because a lipidic vector that carries an overall positive charge (i.e., is cationic) will deliver the nucleic acids nonspecifically, since all cell types have negative-charged membranes. In contrast, an anionic lipidic vector which incorporates a targeting ligand, as discussed above, will deliver the nucleic acid to the targeted cell. These principles pertain, according to the present invention, whether the therapeutic molecule is a DNA, as shown in FIG. 1, or another molecule of therapeutic value.

According to a preferred embodiment of the present invention, the polycation molecule is polylysine (bromide salt, mol. wt. 25,600), which can be purchased from Sigma Chemical Corporation (St. Louis, Mo.). Other polycations can be used, however, including a wide range of short, synthetic cationic peptides. Illustrative of other, suitable polycations are protamine, DEAE-dextran, cationized albumin, polybrene, spermine, polyornithine, histones, a cascade amidoamine "dentritic" polymer, gramicidin S cyclic peptide, and spermidine. Haensler and Szoka, supra.

When an isoelectric complex is formed between the nucleic acid and a polycation, rapid and undesirable aggregation occurs. (In this regard, "isoelectric" connotes a neutral surface potential rather than strict electrical neutrality.) For example, a DNA/polylysine ratio of about 10.47 (wt:wt) is associated with an isoelectric state and, hence, with aggregation. Undesirable aggregation also will occur when slightly charged complexes are formed, especially at high nucleic acid concentrations. Considerably less aggregation occurs when the charge balance between the nucleic acid and the polycation of a complex is far from the isoelectric ratio. Since the DNA/polycation ratio at which isoelectric complexes form changes with pH, a cationic complex can be prepared at a pH where the anionic charge of the nucleic acid is partially neutralized, to increase the cationic/anionic charge ratio.

For example, at pH 2 polylysine is fully protonated and, for a DNA/polylysine ratio of 1:0.75, the cationic charge is greatly in excess. After the complex has formed, the pH can be adjusted to 7.4, where cationic charge is only slightly in excess. This will bring all the polylysine into the complex. No aggregation will occur during the pH adjustment because the complex does not pass through the state where the nucleic acid-to-polycation charge balance is virtually zero ("substantially neutral").

An essentially similar approach applies to the preparation of anionic nucleic acid/polycation complexes, in which case a high pH (for example, about 10) is used to partially neutralize the polycation charge. As a consequence, the overall charge on the complex is shifted away from neutrality during complex formation, avoiding aggregation.

It also is possible, pursuant to the present invention, to affect the charge balance of a complex via other "helper" molecules, i.e., molecules that contribute a charged species or that sequester a charged species in the reaction mixture. Examples of suitable anionic helper molecules include (1) non-monovalent anions such as $PO_4^{3-}$, $HPO_4^{2-}$, EDTA, DTPA, and deferoxamine, (2) anionic polymers such as polymethacrylic acid and poly glutamic acid, and (3) anionic detergents such as cholesteryl hemisuccinate (CHEMS), cholate, fatty acids and deoxycholate. The category of suitable cationic helper molecules is illustrated by (1) non-monovalent cations such as $Ca^{2+}$, $Mg^{2+}$, $Mn^{2+}$, $Al^{3+}$, and spermidine, (2) cationic polymers such as polylysine, DEAE-dextran, spermine, spermidine, protamine, polybrene, cationized proteins, cationic micelles and cationic liposomes, and (3) cationic detergents such as DC-chol, cetyltrimethylammonium bromide (CTAB), etc. (Monovalent cations and anions, such as those introduced via high NaCl used in previous technology, generally are not effective in this context. Adding NaCl increases ionic strength and decreases charge interaction, but does not change the charge balance during complex formation.) Helper molecules can be removed following complex preparation by dialysis or gel-filtration chromatography. The charge of the helper molecule can also be regulated with pH.

After the nucleic acid/polycation complex is formed, it often is useful to bring the complex back to near charge neutrality. This can be achieved, as described above, by addition of an acid or base and by removal or neutralization of a helper molecule.

According to one embodiment of the present invention, the liposome preparation is a DOPE/CHEM 6:4 (w:w) mixture, prepared by standard methods, the pH of which has been adjusted to pH 8.0. Cholesteryl hemisuccinate (CHEMS) can be purchased from Sigma Chemical Company. Dioleoylphosphatidylenthanolamine (DOPE) is available commercially from Avanti Polar Lipids, Inc. (Alabaster, Ala.).

According to another embodiment of the invention, an anionic, non pH sensitive liposome preparation is made consisting of a DOPE/PS (8:2) mixture. Phosphatidyl serine (PS) was purchased from Avanti Polar Lipids.

Any amphiphilic lipid can be used for the lipidic preparation. An example of such a preparation is a composition of anionic liposomes prepared by the methodology of Chu et al., *Pharm. Res.* 7: 824 (1990). other lipidic materials can be substituted to form lipidic vectors such as anionic oil-in-water emulsions or micelles. A lipidic vector of the present invention can be composed of any amphiphiles or their mixtures, such as oil-in-water emulsions and micelles. An example would be the composition Tween 80/CHEMS at a molar ratio of 3:1.

Another step according to the scheme described in FIG. 1 is the addition of a targeting ligand. The targeting ligand can be added to the lipidic vector by mixing in with the anionic lipidic preparation or by conjugation to either the polycation or to a lipid. The methods employed to achieve the conjugation are standard methods, known to one versed in the art.

According to one embodiment of the invention, folate serves as a targeting ligand to the folate receptor ($K_d$=1 nM for folic acid). Folate-PEG-PE (folate-PEG-phosphatidylethanolamine) was synthesized as described previously Lee & Low, *Biochim. Biophys. Acta.* 1233: 134–44 (1995).

According to yet another embodiment of the invention, a fusogenic peptide is added to the lipidic preparation. Fusogenic peptides are amphipathic helix-forming oligopeptides which have been designed to imitate the behavior of the viral fusion peptide. See, for example, Haensler and Szoka, supra.

In a preferred embodiment, an amphipathic helical oligopeptide is incorporated via charge interaction, to serve as a fusogenic peptide. Particularly preferred in this regard is a 20 amino-acid oligopeptide having the sequence GLFGA-IAGFIESILELALEL (SEQ ID NO:1), where the underscored amino acids are negatively charged. The salient features of this non-immunogenic molecule, which can be synthesized by standard methods, are that it is a short peptide (about 20 residues in length) and is non-helical at neutral pH. At the acidic pH 5 or 6, which is commonly found in endosomes, the peptide can undergo a conformational change to an amphipathic alpha helix, which can insert into a cellular membrane and form an aqueous pore. The first eleven residues are identical to the influenza viral fusion peptide N-terminal conserved sequence. The remaining portion contains three negatively charged glutamic acid residues in neighboring positions of a helical wheel which confers to this peptide a pH-sensitive trigger. The negative charge of the glutamic acid residues allows for charge-based interaction with the DNA/polycation complex. A leucine-zipper motif is incorporated into the design of the molecule to allow several of the peptides to interact with each other, facilitating pore formation after membrane insertion.

In accordance with the present invention, the aforementioned 20-mer peptide, with its three negatively charged glutamic acid residues, was added to a positively charged DNA/polylysine complex at a DNA/polylysine/20-mer peptide ratio of 1:0.75:0.4 (wt:wt:wt). The resultant complex then was encapsulated into anionic liposomes composed of DOPE/CHEMS/folate-PEG-PE (6:4:0.01) at a lipid/DNA ratio of 12:1 (wt:wt). These DNA-containing liposomes were highly effective in transfecting receptor-bearing KB cells, and remained effective in the presence of 10% fetal bovine serum. By contrast, liposomes lacking the 20-mer peptide lost transfection effectiveness in the presence of serum.

The present invention is further described by reference to the additional examples below, which are purely illustrative in nature.

EXAMPLE 1

Preparation of Liposome-Based Lipidic Vector Which Encapsulates DNA

Liposome Preparation

Liposomes which were pH-sensitive and which were composed of DOPE/CHEMS (6:4) were prepared by the following method. DOPE and CHEMS (50 mg total lipids) were first dissolved in dry chloroform and then dried into a thin film in a round-bottomed flask. Next, the lipid was suspended in 2.5 ml deionized $H_2O$ by vortexing. The suspension then was adjusted to pH 8 and sonicated in a bath-type sonicator for 5 minutes. The resulting liposomes were sized by light scattering and sterilized by filtration through a 0.45 µm filter. Folate-targeted liposome was prepared by the same method except 0.1 mole % folate-PEG-PE was included in the lipid composition. (Anionic non-pH-sensitive liposome composed of DOPE/PS (8:2) were also prepared by the same method.

Encapsulation of Plasmid DNA into Liposomes

Figure 2:
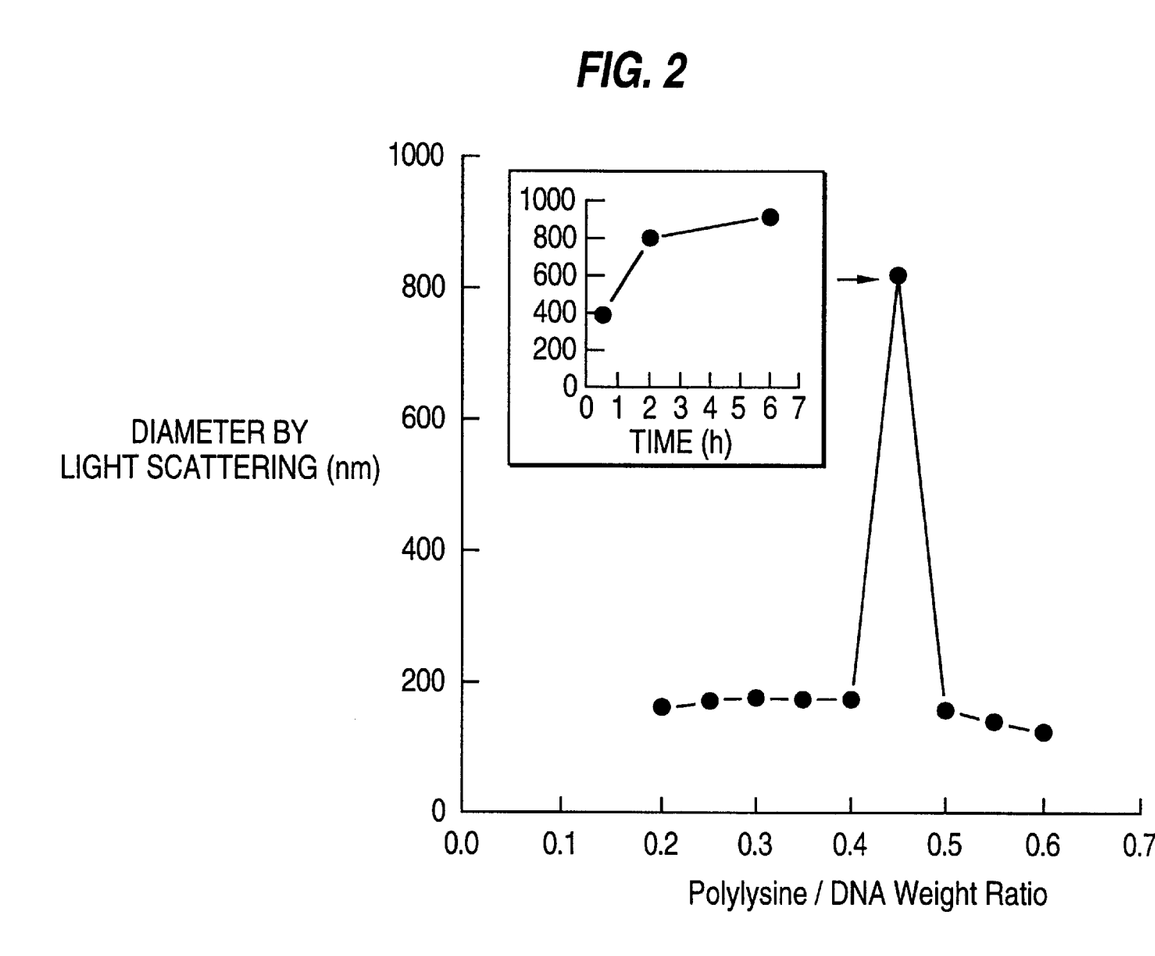
FIG. 2 shows the effect of polylysine/DNA ratio, i.e., the surface charge balance on the stability of DNA/polylysine complex. Particle size was determined on a Coulter N4SD Submicron Particle Analyzer, 2 hours after complex formation. The insert shows that further incubation of the aggregate formed at a polylysine/DNA weight ratio of 0.45 leads to further aggregation.

36 µg poly-L-lysine in 400 µL deionized $H_2O$ was rapidly mixed with 48 µg pRSVluc plasmid DNA, Plautz et al., *Proc. Nat'l. Acad. Sci. USA* 90: 4645–49 (1993), in 400 µL deionized $H_2O$, at DNA/polylysine weight ratio 1:0.75. Aliquots of the resulting DNA/polylysine complex were then rapidly mixed with various amounts of anionic liposomes in equal volumes of deionized $H_2O$.

pRSVluc plasmid DNA and polylysine formed condensed complexes when rapidly mixed. These complexes were stable when the overall charge was either positive or negative (FIG. 2). But when the overall charge was close to neutral, for example, at DNA/polylysine ratio of 1:0.45, rapid aggregation of the complexes occurred (see FIG. 2). In order to determine whether in the presence of excess positive charge all polylysine molecules were involved in DNA complex formation, DNA was mixed with polylysine containing trace amount of fluorescent label in the form of Florecein isothiocyanate (FITC) purchased from Sigma, at a weight ratio of 1:0.75. The resulting DNA/polylysine complex was loaded on the top of a 0 to 30% sucrose gradient in a ultracentrifuge tube. Following 33 min. of centrifugation at 100,000 g, all fluorescence sedimented to the bottom of the gradient suggesting that all polylysine molecules were complexed to DNA (uncomplexed DNA or polylysine remain on the top of the sucrose gradient). The average size of the DNA/polylysine complexes determined by electron microscopy was ~80 nm.

Figure 3:
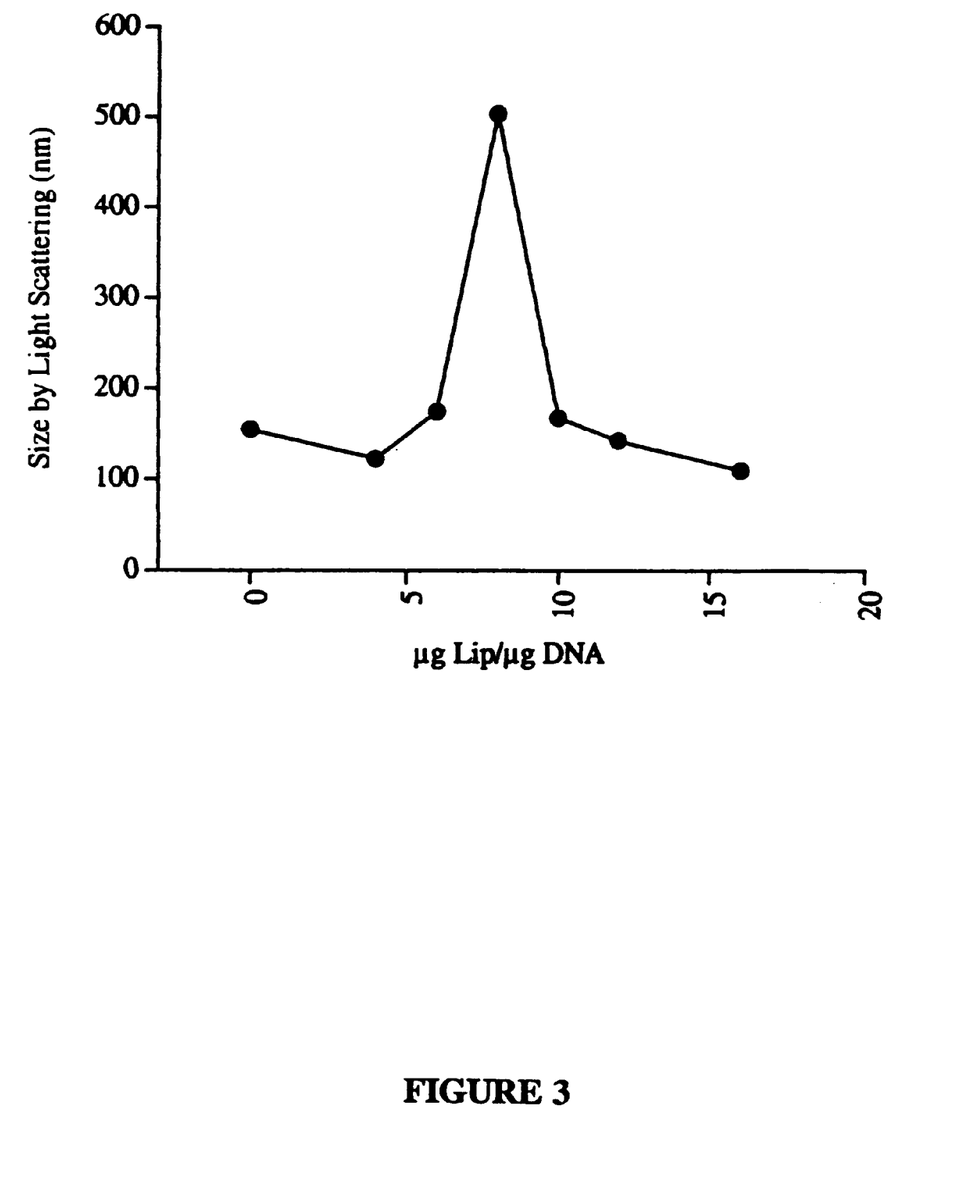
FIG. 3 shows the effect of Lipid/DNA ratio, i.e. overall surface charge, on the stability of the DNA-containing liposomes.

DNA/polylysine (1:0.75) complex became spontaneously encapsulated when rapidly mixed with DOPE/CHEMS (6:4) liposomes. The size of the DNA-containing liposome was dependent on the charge ratio between the DNA/polylysine complex and the anionic liposomes (FIG. 3). When the overall charge was close to neutral, the size of the particles increased over time due to aggregation. A similar charge/size relationship was observed when 0.1 mole % folate-PEG-PE was included in the anionic liposomes during the preparation of folate-targeted liposomes. In order to compare the liposome preparations described above with standard preparations, a cationic liposome DNA/DC-chol complex was prepared according to Gao and Huang, *Biochem. Biophys. Res. Comm.* 179: 280–85 (1991). Its activity was deemed optimum when prepared at a ratio of 1 µg:10 nM of DNA to liposome.

EXAMPLE 2

Lipidic Vector That Incorporates A Targeting Peptide

Transfections

Cells were plated in 24-well plates at $5\times10^4$ cells per well and grown for 24 hr. prior to transfection. To each well, 1 µg plasmid DNA in various formulations was added in 200 µL serum-free culture medium. Following four hours incubation at 37° C., the medium in each well was replaced with medium containing 10% fetal bovine serum. After an additional 36 hours incubation, the cells were lysed in 0 1% Triton X-100 containing 2 mM EDTA. The lysate was assayed for luciferase activity and protein content. Gao and Huang, supra.

Figure 4:
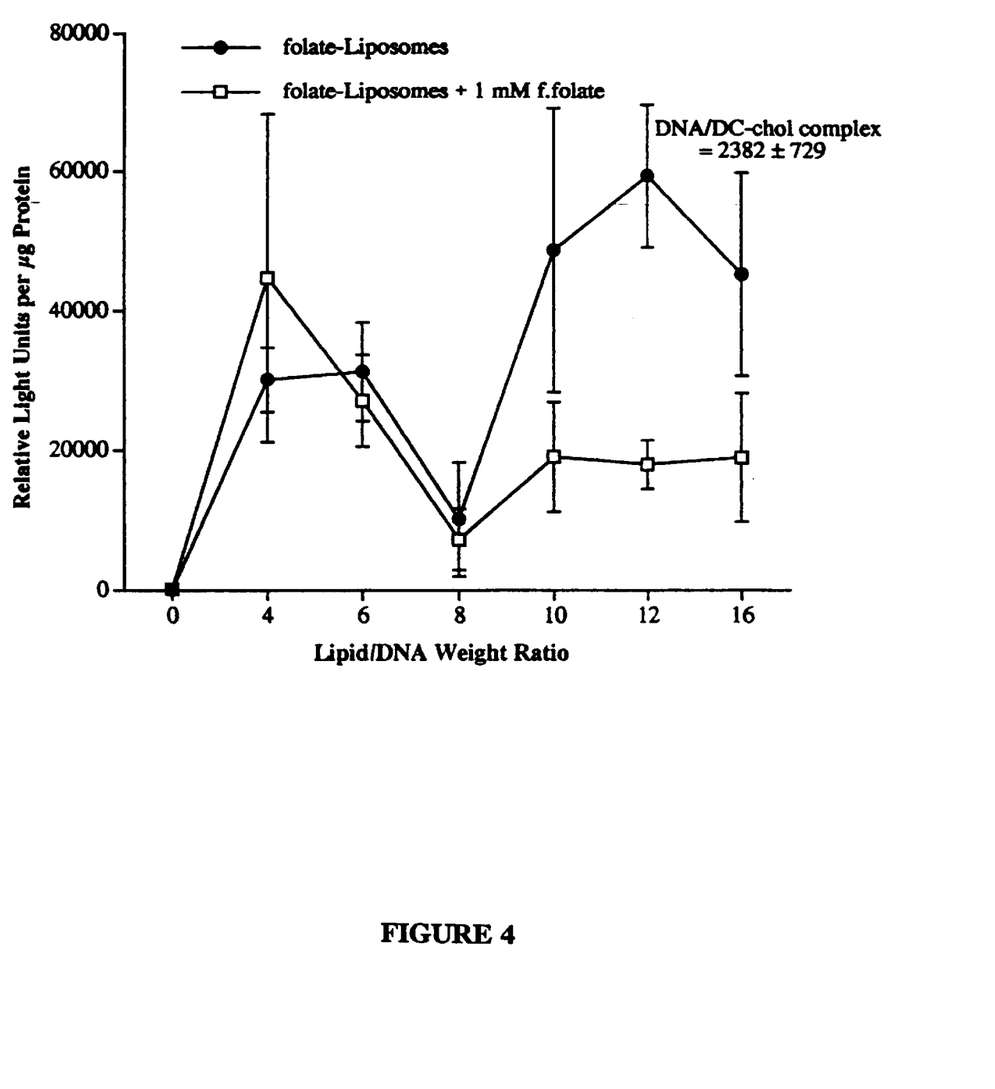
FIG. 4 shows the efficiency of transfection of KB cells, using a DNA encapsulating anionic liposome encapsulating DNA vector which contains a targeting ligand, with liposomes composed of varying lipid/DNA ratios. Transfection efficiency is determined by the level of expression of the luciferase reporter gene. The targeting ligand is folate-PEG-PE. As indicated, the experiment was performed in the presence or absence of 1 mM folic acid. The cationic liposome DNA/DC-chol complex was used at a predetermined optimum ratio of 1 $\mu$g:10 nM and serves here as a standard.

Transfection of Cultured KB Cells with Folate-Conjugated DNA-Containing Liposomes Folate receptor ($K_d$=1 nM for folic acid) has recently been identified as a prominent tumor marker, especially in ovarian carcinomas. KB cells, known to vastly overexpress the folate receptor, were transfected with DNA-containing, folate-targeted liposomes prepared as described in Example 1 (see FIG. 4). At low lipid to DNA ratio (<6), cationic particles were produced. Transfection of the KB cells was efficient but could not be inhibited by the addition of 1 mM free folic acid, which suggested that the cellular uptake was due primarily to charge interaction between the DNA-containing liposomes and the negatively charged cell surface rather than via the folate receptor. At a lipid to DNA ratio of 6, the transfection efficiency with these liposomes was 13-times higher than the cationic liposome DNA/DC-chol complex (prepared under optimized conditions of 1 µg:10 nM DNA/liposome ratio. At higher lipid-to-DNA ratios (>10), where anionic particles were formed, however, transfection appeared to be receptor-mediated, since it could be partially blocked by free folic acid.

Interestingly, even 1 mM folic acid was insufficient to completely block the receptor-mediated transfection. This was probably due to the multivalency of the ligand on the liposomes conferring them much higher affinities than the monovalent folic acid. Non-targeted anionic DNA-containing liposomes were inactive in cellular transfection (data not shown). At lipid to DNA ratios of higher than 12, there was a reduction in transfection activity probably due to DNA uptake competition by excess empty folate-conjugated liposomes.

Figure 5:
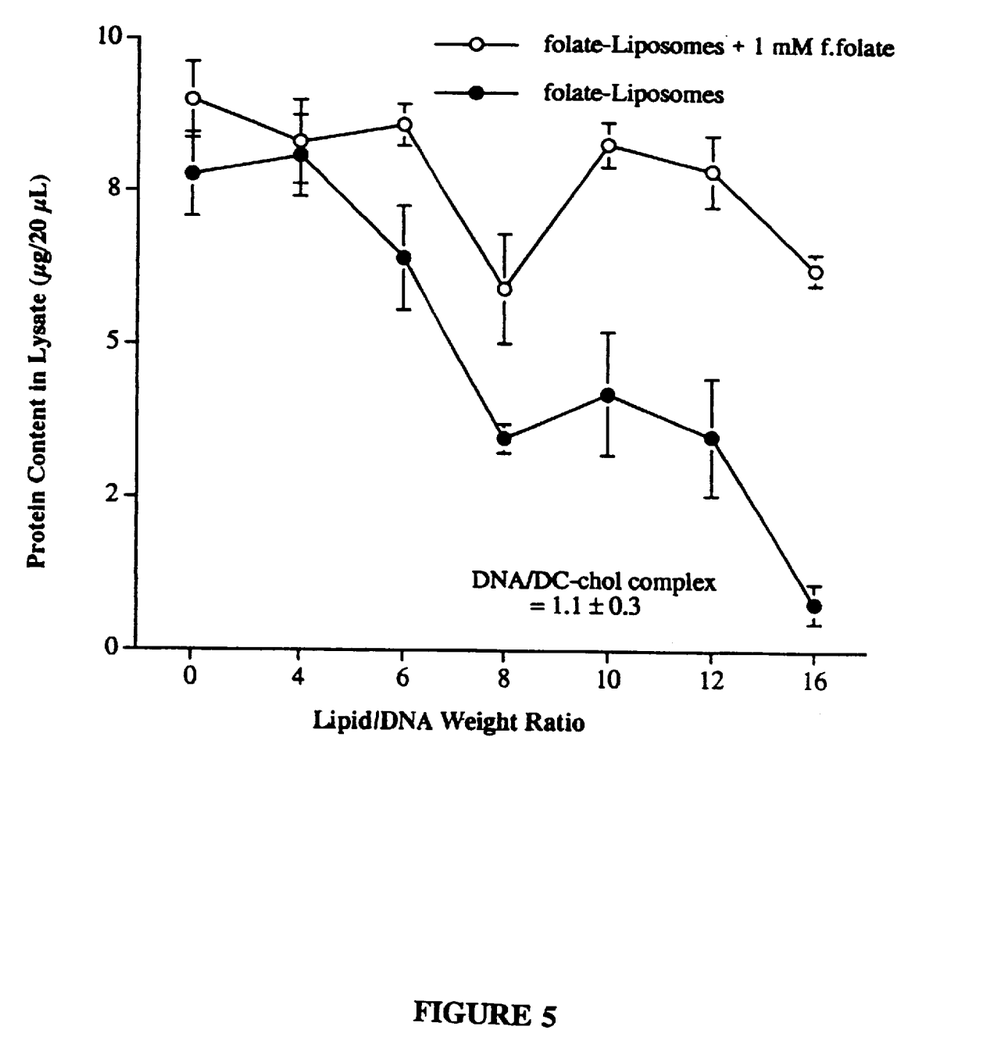
FIG. 5 demonstrates the relative lack of cytotoxicity of the Liposome Encapsulating DNA containing a targeting ligand. The DNA containing liposome and the cationic liposome DNA/DC-chol complex were as those of FIG. 4. The experiment was performed in the presence and absence of 1 mM folic acid, as indicated.
Figure 6:
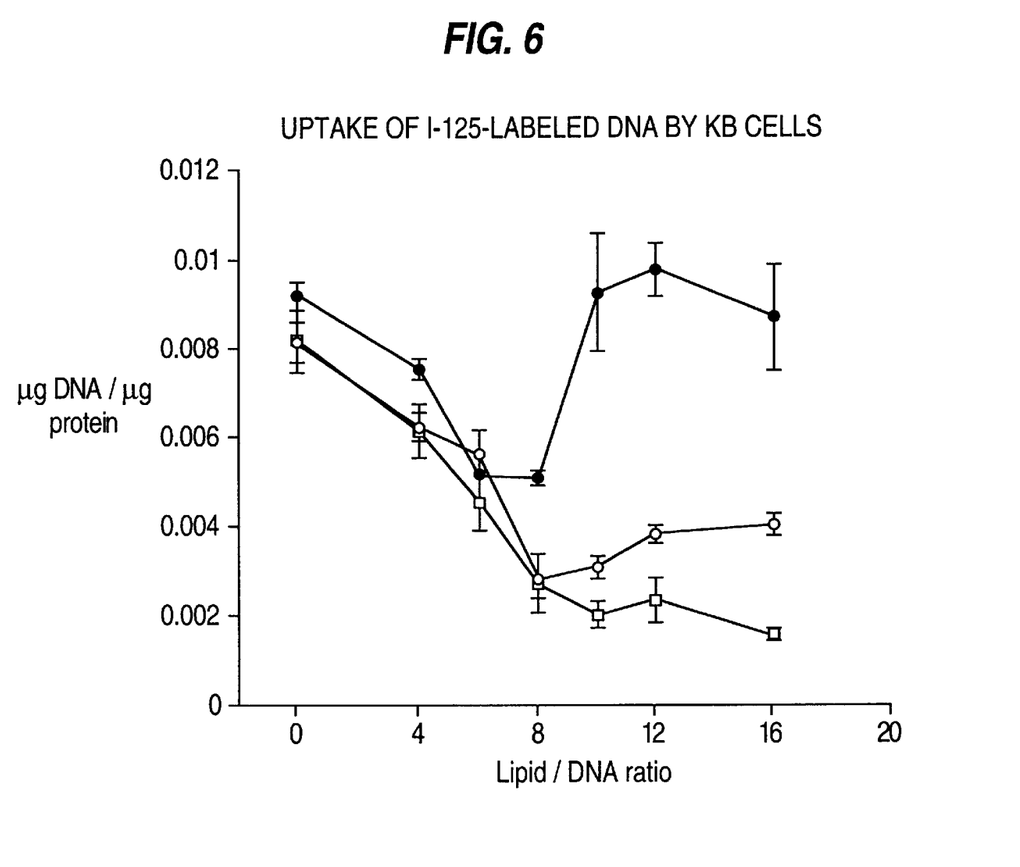
FIG. 6 shows the uptake of $I^{125}$-labeled DNA by KB cells. Cellular uptake of DNA was then determined by counting the radioactivity in the lysate and calibrated with the protein content in the cellular lysate (by the Commassie assay). Open squares are non-targeted DNA-containing liposomes composed of DOPE/CHEMS (6:4); solid circles are folate-targeted liposomes composed of DOPE/CHEMS/folate-PEG-PE (6:4:0.01); open circles are folate targeted liposomes plus 1 mM free folic acid.

The cytotoxicity of various formulations was evaluated by determining the total protein content in the cellular extracts. As shown in FIG. 5, in the cationic range (lipid/DNA<6) DNA-containing liposomes showed very little toxicity compared to cationic liposome DNA/DC-chol complexes. Cells treated with cationic liposome DNA/DC-chol had an 8-fold lower protein level in the extract. Neutral particles (lipid/DNA=8) seemed particularly cytotoxic. In the anionic range (lipid/DNA>10) cytotoxicity was again very low. But very high lipid-to-DNA ratios (>16) led to higher toxicity levels.

By use of these DNA-containing liposomes, similar transfection results also were obtained in HeLa, 2008, BL6, CHO and EL4 cells and T-lymphocytes; a suspension of cultured T-lymphocytes was not transfectable with the cationic liposome DNA/DC-chol complex. Acceptable but slightly lower transfection activity in CHO cells also was obtained when liposomes containing DOPE/phosphatidylserine (8:2), a pH-insensitive anionic lipid composition, were used in place of DOPE/CHEMS liposomes.

EXAMPLE 3

Affecting Targetability of Lipidic Vector

KB cells were seeded at $5\times10^4$ per well in 24-well plates and incubated overnight in a $CO_2$ cell culture incubator. Liposome preparations containing 1 µg $I^{125}$-labeled plasmid DNA and diluted in 200 µL serum-free medium were added in triplicates to each well. After 4 h incubation at 37° C., the cells were washed twice with phosphate-buffered saline (PBS) and lysed in 300 µL lysis buffer. Cellular uptake of DNA then was determined, by counting the radioactivity in the lysate, and calibrated with the protein content, ascertained by Commassie assay, in the cellular lysate. Non-targeted, DNA-containing liposomes composed of DOPE/CHEMS (6:4) were compared with folate-targeted liposomes composed of DOPE/CHEMS/folate-PEG-PE (6:4:0.01) in the presence or absence of 1 mM free folic acid. As can be seen in FIG. 1, for non-targeted liposomes, a high level of cellular uptake took place only at low lipid-DNA ratios, where the overall charge of the DNA-containing liposomes was positive. At these lipid/DNA ratios, folate targeting did not further enhance the level of cellular uptake. At high lipid/DNA ratios (greater than 10:1), however, folate-targeted liposomes are taken up by receptor-bearing KB cells in a ligand-specific manner; that is, the uptake was competitively inhibited by the presence of 1 mM free folic acid.

What is claimed is:

1. A method for creating a lipidic vector for nucleic acid delivery, comprising the steps of
   (A) providing a nucleic acid with a polycation to condense said nucleic acid in a nucleic acid/polycation complex; and
   (B) combining an anionic lipidic preparation with said nucleic acid/polycation complex to form said lipidic vector.

2. A method according to claim 1, wherein a ligand is added to said lipidic vector (i) by covalently bonding said ligand to said anionic lipidic preparation or to said polycation, or (ii) by mixing said ligand with said anionic lipidic preparation or said nucleic acid/polycation complex.

3. A method according to claim 2, wherein said ligand is at least one selected from the group consisting of a tissue-specific ligand, a cellular receptor-targeting ligand, a fusogenic peptide, and a nucleus-targeting peptide.

4. A method according to claim 1, wherein said polycation is selected from the group consisting of (1) a non-monovalent cation; (2) a cationic polymer; and (3) a cationic detergent.

5. A method according to claim 1, wherein said polycation is an acid.

6. A method according to claim 1, further comprising a step of adding a ligand or a combination of ligands selected from the group consisting of (a) a cellular receptor-targeting ligand; (2) a fusogenic ligand; (3) a nucleus-targeting ligand; and (4) a combination of said ligands.

7. A lipidic vector for nucleic acid delivery, said vector being the product of a method according to claim 1.

8. A method according to claim 1, wherein said polycation is selected from the group consisting of: polylysine, protamine, DEAE-dextran, cationized albumin, polybrene, spermine, polyornithine, a histone, a cascade amidoamine dendritic polymer, gramicidin S cyclic peptide, and spermidine.

9. The method according to claim 4, wherein said non-monovalent cation is selected from the group consisting of $Ca^{2+}$, $Mg^{2+}$, $Mn^{2+}$, $Al^{3+}$, spermine and spermidine.

10. The method according to claim 4, wherein said cationic polymer is selected from the group consisting of polylysine, DEAE-dextran, protamine, polybrene, and a cationized protein.

11. The method according to claim 4, wherein said cationic detergent is selected from the group consisting of DC-chol and cetyltrimethylammonium bromide (CTAB).

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 20 amino acids
      (B) TYPE: amino acid
      (C) STRANDEDNESS: single
      (D) TOPOLOGY: linear    (xi) SEQUENCE DESCRIPTION: SEQ ID NO:1:

```
Gly Leu Phe Gly Ala Ile Ala Gly Phe Ile Glu Ser Ile Leu Glu Leu
1               5                   10                  15

Ala Leu Glu Leu
            20
```